United States Patent [19]
Pedersen

[11] Patent Number: 5,838,010
[45] Date of Patent: Nov. 17, 1998

[54] SPATIAL RESOLUTION IMPROVEMENT FOR GAMMA CAMERA

[75] Inventor: Lars M. Pedersen, Horsholm, Denmark

[73] Assignee: General Electric Company, Waukesha, Wis.

[21] Appl. No.: 891,792

[22] Filed: Jul. 14, 1997

[51] Int. Cl.⁶ .......................... G01T 1/161; G01T 1/208
[52] U.S. Cl. ................. 250/369; 250/252.1; 250/363.07; 250/363.09
[58] Field of Search .................... 250/363.04, 363.02, 250/363.07, 363.09, 366, 369, 252.1 A

[56] References Cited

U.S. PATENT DOCUMENTS

| | | | |
|---|---|---|---|
| 5,173,608 | 12/1992 | Motomura et al. | 250/363.04 |
| 5,293,044 | 3/1994 | Klingenbeck-Regn et al. | 250/366 |
| 5,444,253 | 8/1995 | Berlad | 250/363.07 |
| 5,508,524 | 4/1996 | Goldberg et al. | 250/363.07 |

FOREIGN PATENT DOCUMENTS 68581  1/1983  European Pat. Off. .......... 250/363.09

*Primary Examiner*—Edward J. Glick
*Assistant Examiner*—Darren M. Jiron
*Attorney, Agent, or Firm*—Quarles & Brady

[57] ABSTRACT

A method for improving single photo emission computed tomography accuracy by determining photon impact locations within a detector field using PMT intensity signals from all PMTs in an array. The method includes determining the row and column of a PMT which is closest to an impacting photon, subtracting the sum of intensity signals to the left of the identified column from the sum of intensity signals to the right of the identified column generating a differentiated width signal, subtracting the sum of intensity signals above the identified row from the sum of intensity signals below the identified row to provide a differentiated length signal and correlating the differentiated width and length signals with length and width field curves to identify the impact location.

17 Claims, 8 Drawing Sheets

| | C-1 | C-2 | C-3 | C-4 | C-5 | C-6 | C-7 | C-8 |
|---|---|---|---|---|---|---|---|---|
| R-1 | 1 | 1 | 2 | 2 | 1 | 0 | 0 | 0 |
| R-2 | 1 | 1 | 4 | 6 | 1 | 1 | 0 | 0 |
| R-3 | 1 | 4 | 19 | 40 | 4 | 1 | 1 | 0 |
| R-4 | 1 | 8 | 50 | 160 | 12 | 3 | 1 | 1 |
| R-5 | 1 | 4 | 19 | 40 | 4 | 1 | 1 | 0 |
| R-6 | 1 | 1 | 4 | 6 | 1 | 1 | 0 | 0 |

SPATIAL RESOLUTION IMPROVEMENT FOR GAMMA CAMERA

CROSS REFERENCE TO RELATED APPLICATION

Not applicable.

STATEMENT REGARDING FEDERALLY SPONSORED RESEARCH OR DEVELOPMENT

Not applicable.

BACKGROUND OF THE INVENTION

The present invention relates to gamma cameras and more specifically to a gamma camera system for improving the spacial resolution of a detected image by utilizing all generated data.

Single photon emission computed tomography (SPECT) examinations are carried out by injecting a dilution marker comprising a compound labeled with a radio-pharmaceutical into the body of a patient to be examined. A radiopharmaceutical is a substance that emits photons at one or more energy levels. By choosing a compound that will accumulate in an organ to be imaged, compound concentration, and hence radiopharmaceutical concentration, can be substantially limited to an organ of interest. A radiopharmaceutical that emits photons or gamma emissions at a single known energy level is chosen.

While moving through a patient's blood stream the marker, including the radiopharmaceutical, becomes concentrated in the organ to be imaged. By measuring the intensity of the photons emitted from the organ, organ characteristics, including irregularities, can be identified.

To measure photon intensity a planar gamma camera is used. A gamma camera consists of a stand that supports a collimator, a scintillation crystal and a plurality of photomultiplier tubes (PMTS) which form one or more PMT detectors in a single position with respect to a patient. The collimator typically includes a lead block with tiny holes therethrough which define preferred photon paths. The preferred paths are usually unidirectional and perpendicular to the length of the collimator. The collimator blocks emissions toward the crystal along non-preferred paths.

The scintillation crystal is positioned adjacent the collimator on a side opposite the patient and within a prescribed field of view. The crystal absorbs photons that pass through the collimator on a front surface and emits light from a back surface each time a photon is absorbed. For the purposes of this explanation, a photon absorbed by a crystal and emitting light will generally be referred to as an event or a light emitting event and the point of photon impact on the crystal will be referred to as an impact point.

The PMTs are positioned adjacent the crystal and on a side of the crystal opposite the collimator. Light emitted by the crystal is detected by the PMTs which in turn generate analog intensity signals. When a single photon is absorbed by the crystal, the emitted light is typically absorbed by several different PMTs such that several PMTs generate intensity signals simultaneously. The PMT which is closest to the impact point is referred to hereinafter as the event detector. Generally, the event detector emits a signal having the greatest relative intensity although this is not always the case when the point of impact is generally between two PMTs.

A processor receives the PMT signals and deciphers the signals to generate an M by N array of data called pixels. Together the array of pixel information is used by the processor to form an emission image corresponding to the specific camera position.

During deciphering, PMT signal intensities corresponding to each event are deciphered in an effort to precisely determine where in the field of view the event occurred. Once all locations of individual events have been identified, the processor can use the precise locations to create an image of the organ of interest.

There are several methods used to convert PMT signal intensities into an image and the different methods can be distinguished by image quality. Clearly, the least difficult image to generate would include only a relatively small number of pixels corresponding to the number of PMTs. For example, where there are forty-eight PMTs comprising eight columns and six rows, a forty-eight pixel image could be generated by simply determining which PMT signal intensity is the greatest for each event. While easy to generate, such an image would be useless as it would not reveal sufficient information for a radiologist to identify image components.

To provide useful images, the image granularity must be greater than the number of PMT tubes. Thus, imaging methods must be able to determine where, adjacent a PMT's width and length, a light emitting event occurs. Hereinafter the point along a PMT's width and length where an event occurs will be referred to as an impact location.

One imaging method, known as the Anger method, has been used extensively to increase SPECT image accuracy by better identifying impact locations. According to this method, after an event detector is identified, to determine where the impact location is within the PMT's width, several PMT signal intensities on either side of the event detector are mathematically combined.

Figure 1:
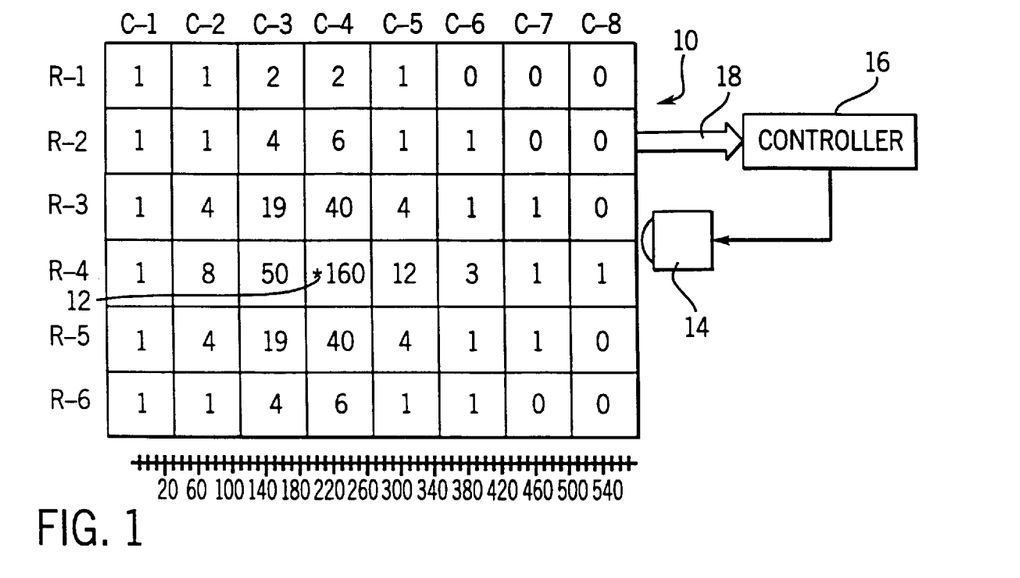
FIG. 1 is a plan view of an array of photomultiplier tubes (PMTs)

For example, referring to FIG. 1, a forty-eight element PMT array 10 is illustrated including eight columns C-1 through C-8 and six rows R-1 through R-6. Assuming an actual impact location corresponding to a single event is located at the point identified by numeral 12, PMT signal intensities might be as indicated in each of the PMT tubes. As expected, because the event occurred adjacent PMT R-4, C-4, the signal intensity for that PMT is the greatest and intensities as the distance from that tube increases become less and less. Also, as expected, because impact location 12 is closer to column C-2 than to column C-4, the intensity signal magnitude for PMT C-3, R-4 is greater than the magnitude for PMT C-5, R-4. Because impact location 12 is equidistant from rows R-3 and R-5, intensity signal magnitudes in PMTs C-4, R-3 and C-4, R-5 are identical.

According to the Anger method, to determine where the impact location is within the width of PMT R-4, C-4, the PMT signal intensity of the PMT directly to the left of PMT R-4, C-4 is added to the PMT signal intensities above and below the PMT directly to the left of PMT R-4, C-4 to generate a first composite signal (i.e. signal intensities from PMT R-3, C-3; PMT R-4, C-3; and PMT R-5, C-3 are added). In addition, the PMT signal intensity of the PMT directly to the right of PMT R-4, C-4 is added to the PMT signal intensities above and below the PMT directly to the right of PMT R-4, C-4 to generate a second composite signal (i.e. signal intensities from PMT R-3, C-5; PMT R-4, C-5; and PMT R-5, C-5 are added). Then, the first and second sums are compared to determine where the impact location is within the PMT width.

In the present example the Anger method would yield a first composite signal of 88 and a second composite signal of 20. Comparing the two sums indicates that the impact location is closer to the left hand side of PMT R-4, C-4 than to the right and specifically, where the entire width of PMT R-4, C-4 is taken to be unity (i.e. 1), the impact location is 0.1852 P.U. from the lefthand side thereof (i.e. second composite signal/first+second composite signals=20/108). This same protocol can be used to determine where the impact location is along the PMTs length (perpendicular to the width).

The accuracy of any location determining method can be investigated according to a test protocol providing a photon source at known locations with respect to a PMT detector and comparing the calculated impact location with the known location. For example, in the example above, if a photon source had been placed 0.1852 P.U. from the left hand side of detector C-4, R-4, and the data above was generated, the Anger method would be 100% accurate for photons impacting the detector at that position. Unfortunately, the Anger method is not 100% accurate and thus, the industry has sought other methods to improve accuracy.

Another method to determine impact location which is more accurate than the Anger method, is generally referred to as the row/column method. This method is similar to the Anger method except that more than six signal intensities are used to determine the impact location within each PMT width or column. Specifically, according to this method, to determine where an impact location is along the width of an event detector, all signal intensities from PMTs in the first column to the left are added to generate a first composite signal and of the event detector all signal intensities from PMTs in the first column to the right of the event detector are added to generate a second composite signal. The first and second composite signals are compared to determine impact location.

Referring again to FIG. 1, according to the row/column method all signal intensities in column C-3 are added generating the first composite signal and all signal intensities in column C-5 are added generating the second composite signal. In this case, the first composite signal is 98 and the second composite signal is 23. When compared, the first and second signals indicate that, assuming PMT width to be unity, the impact location is 0.1901 P.U. from the lefthand side thereof (i.e. second composite signal/first+second composite signal=23/121). This same protocol is used to determine where the impact location is within the PMT length.

Using the test protocol described above, it has been proven that the row/column method is more accurate than the Anger method. The increased accuracy of the row/column method is primarily attributable to the fact that more signal intensity information is used to generate the row/column impact location than to generate the Anger impact location. For this reason, and also because the row/column method does not require additional hardware (i.e. it can be implemented in software), the row/column method has been the method of choice.

Unfortunately, even the row/column method is insufficiently precise to provide image detail needed for some diagnostic procedures. Therefore, it would be advantageous to have an even more precise imaging method for use in SPECT imaging which is inexpensive to implement.

SUMMARY OF THE INVENTION

The present invention includes a method to be used with a gamma camera for improving the quality of generated images by utilizing all generated image data to increase the accuracy of identified impact locations. Because more data is used, "photon" statistics are improved. In this way the granularity of the resulting image is improved and diagnostic analysis is more precise.

To this end, the inventive method is to be used with a gamma camera, the camera including a scintillation crystal having opposite impact and emitter sides and a plurality of light detecting photo multiplier tubes (PMTs), each PMT having a width and a length and arranged end to end along their widths in Y rows forming X columns on the emitter side. The crystal is positionable adjacent an imaging area such that photons from within the imaging area impact the impact side, each photon which impacts the impact side impacting the side at a specific impact point adjacent a specific impact location on an event PMT. The event PMT is the PMT having the impact point associated with a specific photon, when a photon impacts the crystal, the crystal emitting light from the emitter side adjacent the impact point, the PMTs sensing emitted light and generating intensity signals related to each impacting photon. The method comprising the steps of, when a photon impacts the crystal, determining the event PMT, determining an event column, the event column being the column in which the event PMT is located, mathematically combining the intensity signals of all PMTs to a first side of the event column providing a first composite signal, mathematically combining the intensity signals of all PMTs to a second side of the event column providing a second composite signal and comparing the first and second composite signals to determine the impact location along the width.

Preferably, the method is also for determining where an impact location occurs along the event PMT's length. To this end, the method further including the steps of, after determining the event PMT, determining an event row, the event row being the row in which the event PMT is located, mathematically combining the intensity signals of all PMTs on a first side of the event row providing a third composite signal, mathematically combining the intensity signals of all PMTs on a second side of the event row providing a fourth composite signal and comparing the third and fourth composite signals to determine the impact location along the length.

Also, preferably, the total widths of the PMTs form a width field and the step of comparing the first and second composite signals includes the steps of subtracting the first composite signal from the second composite signal to produce a total signal and correlating the total signal with a field position to determine an impact location estimate along the width.

Thus, one object of the invention is to provide a simple method whereby photon statistics can be improved to provide more precise impact locations and improve SPECT images. To this end, all detected light intensity is utilized to determine photon impact location and thereby determine the impact point on the adjacent crystal. Referring again to FIG. 1, using the present method, the signal intensities to the left of PMT R-4, C-4 add providing 1036 while the signal intensities to the right add providing 399 resulting in an impact location within PMT R-4, C-4 of 0.2780 P.U. from the left hand side of the PMT. Using the protocol above to investigate methodology accuracy, it has been proven that this impact location is more accurate than the locations identified using either the Anger or the row/column methods described. Hereinafter the inventive method will be referred to generally as the "super correlated method" or simply the "correlated method."

Another object is to provide more precise images without appreciably increasing detector and system costs. To this end, the correlated method can be implemented in software using conventional hardware. All signal intensities are already provided by existing hardware and additional computations required to increase image quality are minimal.

In one aspect the method may include the step of, after the impact location estimate is determined, determining a correction value for the location estimate and adjusting the location estimate as a function of the correction value.

Although the inventive method is relatively more accurate than either the Anger or row/column method, impact locations are still not 100% accurate according to the test protocol described above. This is particularly true with respect to PMTs nearest the edges of the array 10 in FIG. 1. This is because, at the edges, the amount of intensity data generated is reduced on one side of an event PMT and is increased on the opposite side. For example, referring again to FIG. 1, if the photon which impacted the crystal at point 12 adjacent PMT C-4, R-4, had actually impacted the crystal adjacent PMT C-2, R-4, only one column C-1 of the left of PMT C-2, R-4 would generate data and six columns C-3 through C-8 to the right would generate data. When composite signals are generated and compared the resulting impact location would be further to the right than the actual location.

To correct for such location errors, prior to imaging the test protocol identified above can be used to generate correction values for each impact location. To this end, during a commissioning procedure a photon source is placed in known locations with respect to the array 10. The inventive correlated method is used to calculate impact locations for each known location. A look-up table is generated which correlates the calculated impact locations and the known locations. Then, during imaging, after an impact location is calculated, the calculated location is correlated with a known location in the look-up table and the known location is recorded as an actual location for imaging purposes.

The invention also includes an apparatus to be used with a gamma camera, the camera including a scintillation crystal having opposite impact and emitter sides and a plurality of light detecting photo multiplier tubes (PMTs), each PMT having a width and a length, the PMTs arranged end to end along their widths in Y rows forming X columns on the emitter side, the crystal positionable adjacent an imaging area such that photons from within the imaging area impact the impact side, each photon which impacts the impact side impacting the side at a specific impact point adjacent a specific impact location on an event PMT, the event PMT being the PMT having the impact point associated with a specific photon, when a photon impacts the crystal, the crystal emitting light from the emitter side adjacent the impact point, the PMTs sensing emitted light and generating intensity signals related to each impacting photon, the apparatus for determining where an impact location occurs along an event PMT's width. The apparatus includes a calculator for determining an event PMT and an event column, the event column being the column in which the event PMT is located, a first summer for mathematically combining the intensity signals of all PMTs to a first side of the event column providing a first composite signal, a second summer for mathematically combining the intensity signals of all PMTs to a second side of the event column providing a second composite signal and a comparator for comparing the first and second composite signals to determine the impact location along the width.

Preferably, the apparatus is also for determining where an impact location occurs along an event PMT's length, the comparator being a first comparator and the calculator also identifying an event row, the event row being the row in which the event PMT is located. In this case, the apparatus further comprises a third summer for mathematically combining the intensity signals of all PMTs on a first side of the event row providing a third composite signal, a fourth summer for mathematically combining the intensity signals of all PMTs on a second side of the event row providing a fourth composite signal and a second comparator for comparing the third and fourth composite signals to determine the impact location along the length.

Also, preferably, the calculator is a first calculator, the total widths of the PMTs form a width field and the comparator includes a second calculator for mathematically combining the first and second composite signals to produce a total signal and correlating the total signal with a field position to determine an impact location estimate along the width. Correlation may be facilitated through a look-up table.

The invention also includes a method to be used with a gamma camera signal processor, the camera including a scintillation crystal having opposite impact and emitter sides and at least X by Y light detecting PMTs arranged end to end along PMT widths in X columns and Y rows on the emitter side, the total width of the PMTs in a row defining a view width, the crystal positionable adjacent an imaging area such that photons from within the imaging area impact the impact side at specific impact points adjacent specific impact locations on the PMTs. When a photon impacts the crystal, the crystal emits light from the emitter side adjacent the impact point, the PMTs sense emitted light and generate intensity signals related to each impacting photon. The method is for calibrating the signal processor to correlate signal intensities with impact locations within an event PMT's width, an event PMT being the PMT adjacent an impact point. The method includes the steps of moving a photon point source from one end of the view width to the other, detecting and recording signal intensities as a function of point source location along the view width providing a separate intensity curve for each PMT, adding up the signal intensities in each column generating a separate column intensity signal for each column, for at least each individual column in the subset of columns consisting of the second through the (X-1)th, generating a differentiated curve consisting of all intensity curves corresponding to columns to a first side of the individual PMT being subtracted from all intensity curves corresponding to columns to a second side of the individual PMT, choosing segments of each differentiated curve which are essentially the same width as corresponding PMTs to be discriminated segments and offsetting the discriminated segments to provide an essentially continuous field width curve.

In one aspect, the total lengths of the PMTs in each of the Y rows define a field of view length, the method further includes the steps of moving the photon point source from one end of the view length to the other, detecting and recording signal intensities as a function of point source location along the view length providing a separate intensity curve for each PMT, adding up the signal intensities in the separate rows to generate row signal intensities, for at least each individual row in the subset of rows consisting of the second through the Y-1 rows, generating a differentiated curve consisting of all intensity curves corresponding to rows a first side of the individual row being subtracted from all intensity curves corresponding to rows to a second side of the individual row, choosing segments of each differentiated curve which are essentially the same length as corresponding PMTs to be discriminated segments and offsetting the discriminated segments to provide an essentially continuous field length curve.

Thus, one other object of the invention is to provide a simple method of calibrating a signal processor for quickly determining impact location within a PMT's width and length as a function of sensed intensity signals. This method provides two continuous curves on perpendicular axis which are easy to use to determine impact location.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

DETAILED DESCRIPTION OF THE INVENTION

A. Theory

Simply put, the present invention is based on the premise that impact location and impact point accuracy with gamma cameras can be increased by utilizing all intensity data collected by a gamma camera. Thus, referring again to FIG. 1, while the Anger method described above only utilizes intensity signals from six of the forty-eight PMTs and the rows/column method utilizes intensity signals from twelve of the forty-eight PMTs, the present invention utilizes intensity signals from a total of forty-two of the forty-eight PMTs to generate accurate impact locations within a column and then uses forty-two intensity signals to generate accurate impact location within a row.

To this end, during a commissioning procedure prior to imaging, two separate field curves are derived. A first field curve is a field width curve which corresponds to the width of a detector. The width curve plots impact location along the width of a detector as a function of a differentiated intensity signal derived from all simultaneous PMT intensity signals. During an imaging period, after an event PMT is identified wherein the event PMT is the PMT which includes an impact location corresponding to an impact point caused by a specific photon on a scintillation crystal, a differentiated signal corresponding to the specific photon is derived by subtracting the total value of intensity signals from a first side of the event PMT from the total value of intensity signals from a second side. The differentiated signal is correlated with the width curve to identify the impact location along the event PMTs width.

The second field curve is a field length curve which corresponds to the length of a detector. The length curve plots impact location along the length of a detector as a function of a differentiated signal. Again, during an imaging period a differentiated signal corresponding to a specific photon is derived and then used to find an impact location within an event PMT, along the length dimension of a detector. Derivation of the width and length curves is described in the following commissioning procedure section.

While the inventive method must be used twice for each photon impact, once to determine impact location along detector width and once to determine impact location along detector length, because the method is essentially identical in both operations, the method will only be explained in detail with respect to the width dimension.

As in most SPECT operations, while light gathered by PMTs on the edges of a detector, referred to hereinafter as edge PMTS, is used to determine "impact locations in other PMTS, impact locations within edge PMTs are disregarded in the present method such that the total imaging field dimensions are reduced considerably. For the purposes of this explanation, it will be assumed that the total effective detector width during imaging is 540 mm with 50 mm of width on the distal edges of detectors in columns C-1 and C-8 disregarded.

B. Commissioning Procedure

The commissioning procedure includes two separate protocols. A first protocol includes generating separate width and length field curves which plot differentiated column and row intensity signals, respectively, as a function of impact location along the width and length of a detector, respectively. The second protocol includes a method to correct for errors in the width and length field curves by calculating impact locations using the field curves and correlating the calculated locations with known correct locations.

1. Generating Field Curves

Referring again to FIG. 1, for the purposes of this explanation it will be assumed that the width and length dimensions of each PMT C-1, R-1 through C-8, is 80 mm×80 mm so that the total width and length dimensions of an 8×6 detector is 640 mm×480 mm. Referring also to the commissioning method 72 depicted in FIG. 2, during the first step 74, a controller 16 is used to move a gamma source 14 which is directed at array 10 from one side of array 10 to the other cutting across each column C-1 through C-8 between rows R-3 and R-4. The source 14 generates single photons. As source 14 is moved across array 10, controller 16 generates and records column intensity signals for each of columns C-1 through C-8 as a function of source location along the 540 mm width field.

Figure 2:
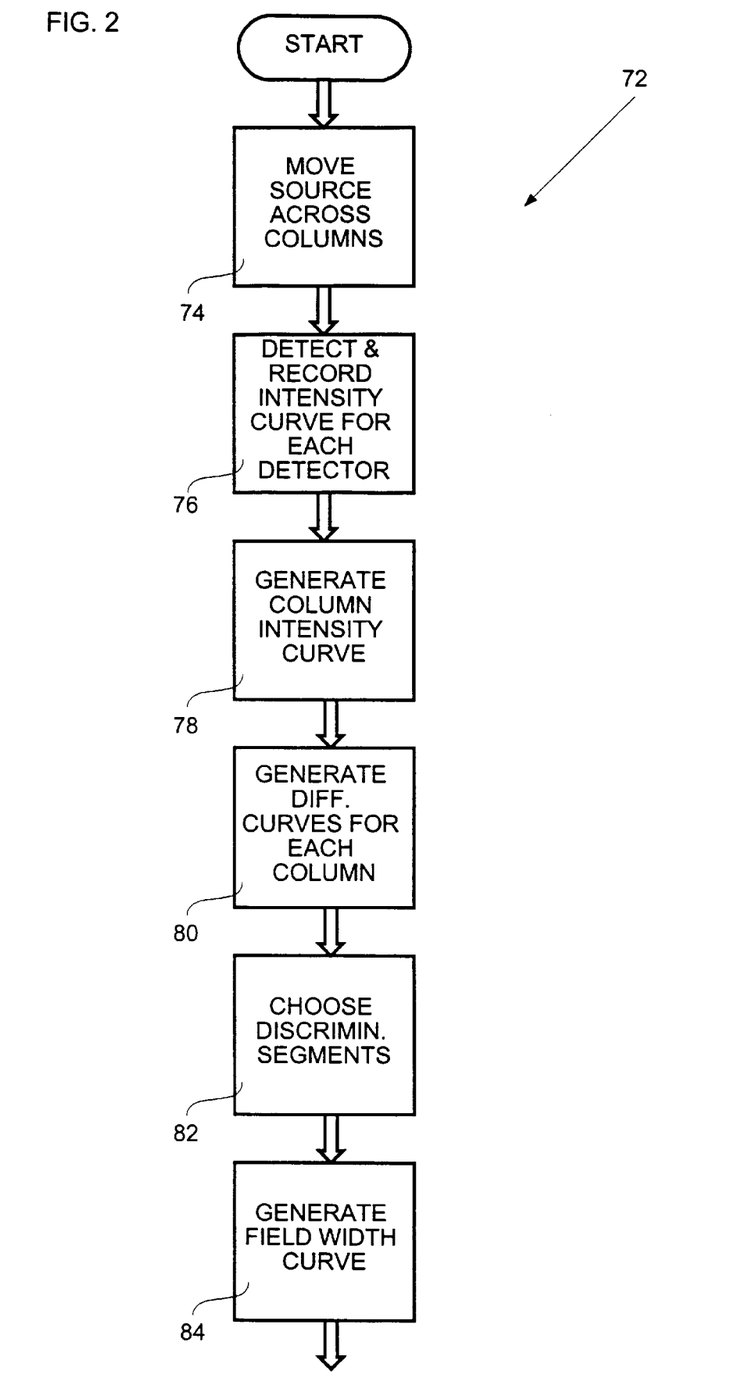
FIG. 2 is a flow chart illustrating an inventive commissioning procedure.

To this end, first, at block 76, controller 16 receives intensity signals from each PMT in array 10 via a bus 18 and records the intensity signals as separate intensity curves for each of the forty-eight PMTs. Each intensity curve includes intensity data as a function of source position along the 540 mm effective detector width. Each PMT intensity curve is parabolic having a peak amplitude when the source is aligned with a PMT's column and reduced amplitudes on either side thereof. For example, the curve for PMT C-4, R-4 will have a minimal amplitude when the source is above either of columns C-1 or C-8 and will have a maximum amplitude when the source is above column C-4.

Figure 3:
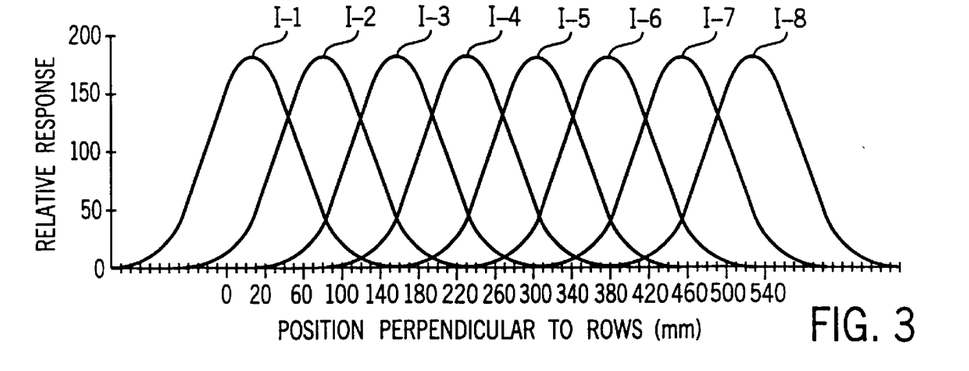
FIG. 3 is a graph illustrating relative response of PMTs in columns C1 through C8 in FIG. 1 as a gamma source is moved there across from column C1 through column C8.
Figure 4:
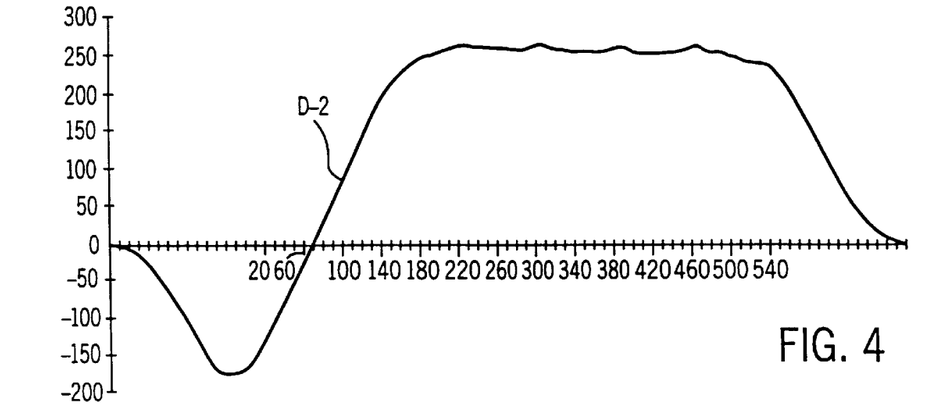
FIG. 4 is a graph illustrating a differentiated relative response about column C2 in FIG. 1.
Figure 5:
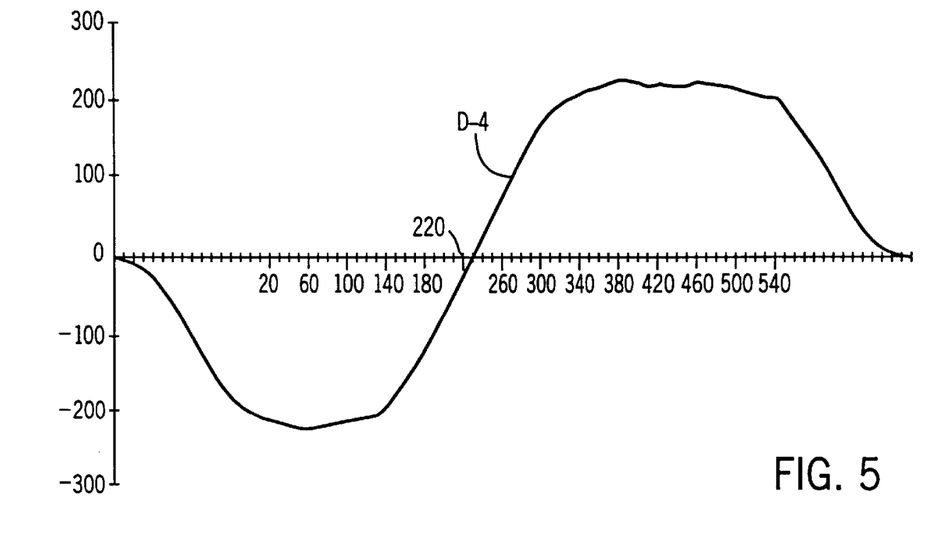
FIG. 5 is similar to FIG. 4 except that the response is about column C4 in FIG. 1.

Second, after curves for each PMT have been generated and stored, controller 16 uses the PMT intensity curves to generate column intensity curves at block 78. To this end, the controller sums the PMT intensity curves in each column producing eight parabolic column intensity cures I-1 through I-8 as illustrated in FIG. 3. In FIG. 3 (as well as in FIGS. 3 through 7), all curves I-1 through I-8 are plotted as a function of location along the 540 mm detector width. The ordinate axis in FIG. 3 (and FIGS. 4 through 6) represents intensity values in intensity units IU).

Figure 6:
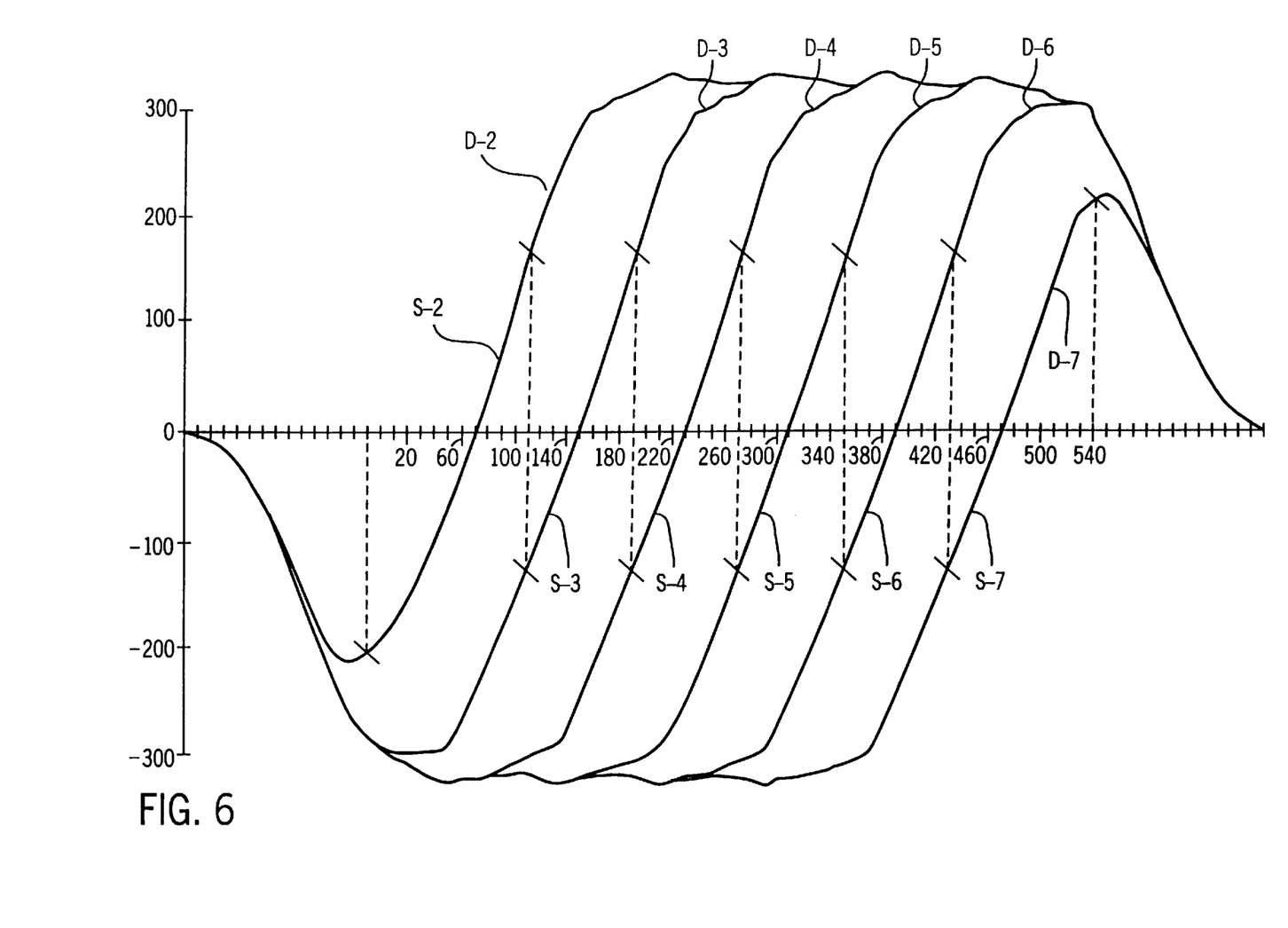
FIG. 6 is a graph illustrating differentiated relative responses about each of columns C1 through C4 in FIG. 1.

At block 80, the controller uses the column intensity curves I-1 through I-8 to generate differentiated curves corresponding to each of columns C-2 through C-7. To generate a differentiated curve for a specific column, the intensity curve I-2 through I-7 corresponding to the specific column C-2 through C-7 is removed from FIG. 3 and the column intensity curves to the left of the specific column are subtracted from the curves to the right of the specific column. For example, referring to FIGS. 1, 3, and 4, to generate a differentiated curve D-2 corresponding to column C-2, column intensity curve I-2 is removed from FIG. 3, curve I-1 (to the left of the curve I-2) is inverted (i.e., subtracted) and curves I-3 through I-8 are summed) generating curve D-2. As another example, referring to FIGS. 1, 3, and 5, to generate a differentiated curve D-4 corresponding to column C-4, column intensity curve I-4 is removed from FIG. 2, curves I-1 through I-3 are inverted (i.e., subtracted) and summed and curves I-5 through I-8 are summed. Differentiated curves D-2 through D-7 for each of columns C-2 through C-7 are illustrated in FIG. 6. Differentiated curves have not been provided for columns C-1 and C-8 because those columns do not include adjacent columns on both sides.

Referring to FIGS. 2 and 6, next, at block 82, controller 16 selects discriminated segments S-2 through S-7 from each of the differentiated curves D-2 through D-7. Segments S-2 through S-7 are defined in FIG. 6 by the area between hash marks on each of the curves D-2 through D-7, respectively. The run (i.e. horizontal component along an abscissa axis) of each discriminated segment S-3 through S-6 is equal to the width of a corresponding column C-3 through C-6, respectively. For example, referring to FIGS. 1 and 6, column C-3 extends from approximately 110 mm to 190 mm and likewise the run of discriminated segment S-3 extends from approximately 110 mm to 190 mm.

In the present example the rise (i.e. vertical component along an ordinate axis) of each discriminated segment S-3 through S-6 is approximately 260 IUs and passes through zero at a point approximately midway along its length. For the purposes of this explanation it will be assumed the rise of each segment S-3 through S-6 is precisely 260 units and each passes through zero precisely at its midpoint. The runs and rises of segments S-2 and S-7 are slightly longer so that segments S-2 and S-7 extend well into columns C-1 and C-8.

Once segments S-2 through S-7 have been chosen they are vertically offset such that a continuous curve results which intersects zero in the middle of the 540 mm width. To this end segments S-5, S-6 and S-7 are shifted upward by 130, 390 and 650 IUs, respectively, while segments S-2, S-3 and S-4 are shifted downward by 130, 390 and 650 IUs, respectively, generating segments S-2' through S-7' in FIG. 7. When so shifted, segment S-2' begins at coordinates: intensity=–810, location= 0 and ends at intensity=–520, location=110; segment S-3' begins at coordinates: intensity= –520, location=110 and ends at intensity=–260, location= 190; segment S-4' begins at coordinates: intensity=–260, location=190 and ends at intensity=0, location=270; segment S-5' begins at coordinates: intensity=0, location=270 and ends at intensity=260, location=350; segment S-6' begins at coordinates: intensity=260, location=350 and ends at intensity=520, location=430 and segment S-7' begins at intensity=520, location=430 and ends at intensity=810, location 540 mm. Thus, segments S-2' through S-7' form a continuous width curve 86 which stretches across the entire width field of detector array 10 and which can be used to approximate impact location along the 540 mm width field.

Figure 7:
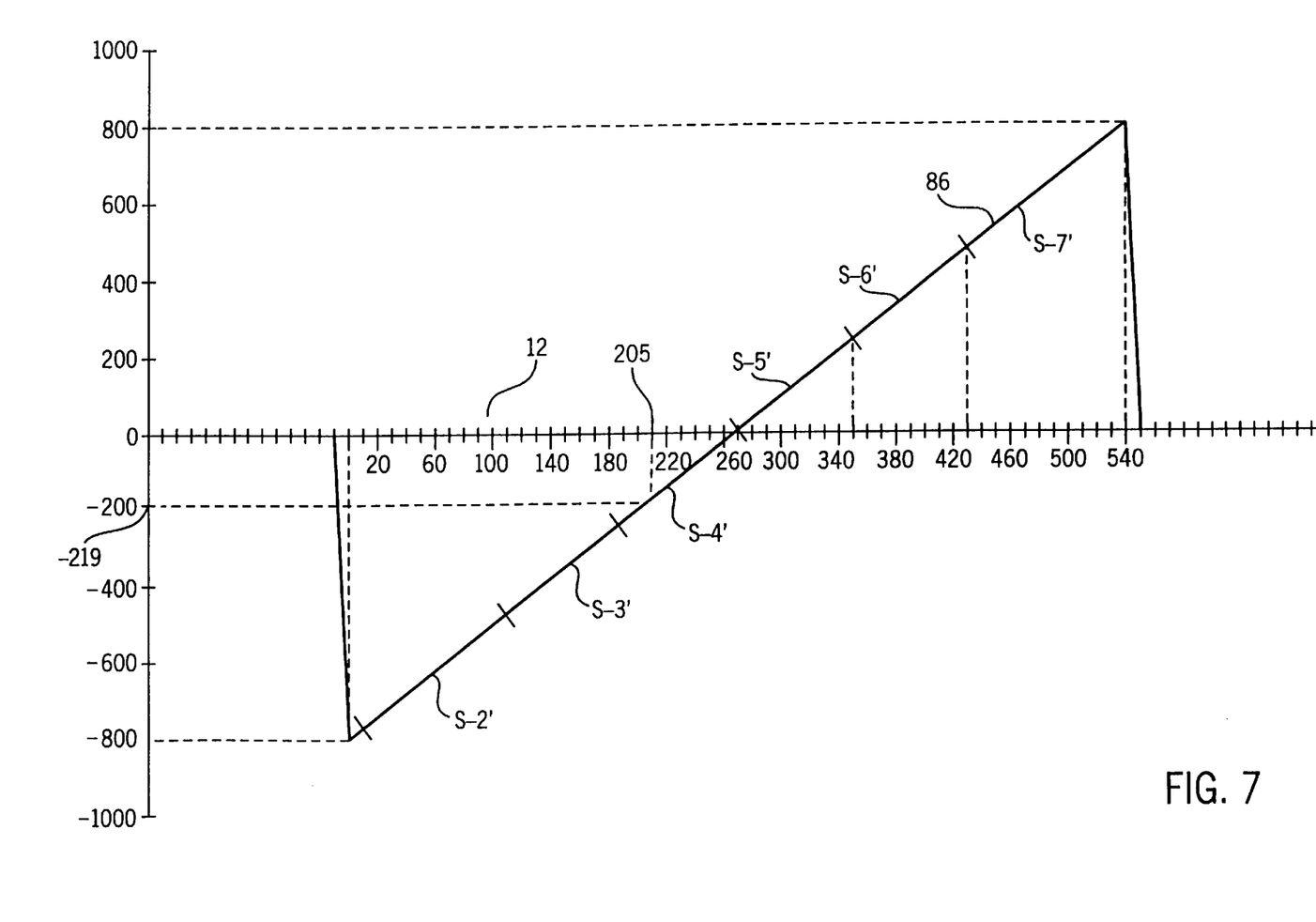
FIG. 7 is a graph illustrating a position curve generated according to the present invention.

Although not illustrated, during the commissioning period a second field curve which is similar to the curve in FIG. 7 is generated, this time by generating row intensity curves like the column curves of FIG. 3 and differentiated curves (see FIGS. 4 and 5) from the row curves, selecting discriminated segments (FIG. 6) from the differentiated curves and offsetting the segments to provide an essentially linear length field curve which extends across the entire 380 mm effective length of the detector. Note that, in addition to effects of PMT irregularities, the width and length field curves will be different because there are fewer rows than columns in the example. Thus, while eight column intensity curves I-1 through I-8 (FIG. 3) and six differentiated curves D-2 through D-7 (FIG. 6) where generated to provide the width field curve 86, only six column intensity curves corresponding to rows R-1 through R-6 and four differentiated curves corresponding to rows R-2 through R-5 are used to generate the length curve.

2. Correcting Field Curves

Referring still to FIG. 7, curve 86 is not linear. The non-linearity reflects the fact that there is still some impact location error despite increased photon statistics. Therefore, the commissioning period also includes second correction protocol.

To this end, controller 16 is used to move source 14 to various locations adjacent array 10. As source 14 is moved, controller 16 does several things. First, controller 16 records the known source positions during movement.

Second, at each source position, controller 16 receives all PMT intensity signals via bus 18 and uses the width field curve (FIG. 7) and the length field curve (not illustrated) to generate an estimated impact location as a function of the PMT intensity signals.

Third, controller 16 correlates each estimated impact location with the known source location generating a look-up table of estimated and actual impact locations. During this procedure controller 16 may generate several hundred estimated impact locations, each consisting of both length and width locations within an associated PMT. Once several hundred estimates have been generated and correlated with actual locations, controller 16 can truncate the estimates and actual locations to provide several thousand correction values, each corresponding to a different width/length location within the detector field. The correction values and estimated values are provided in a look-up table for use by a correction module 112 (FIG. 11) which is described in more detail below.

C. Hardware Configuration

Figure 8:
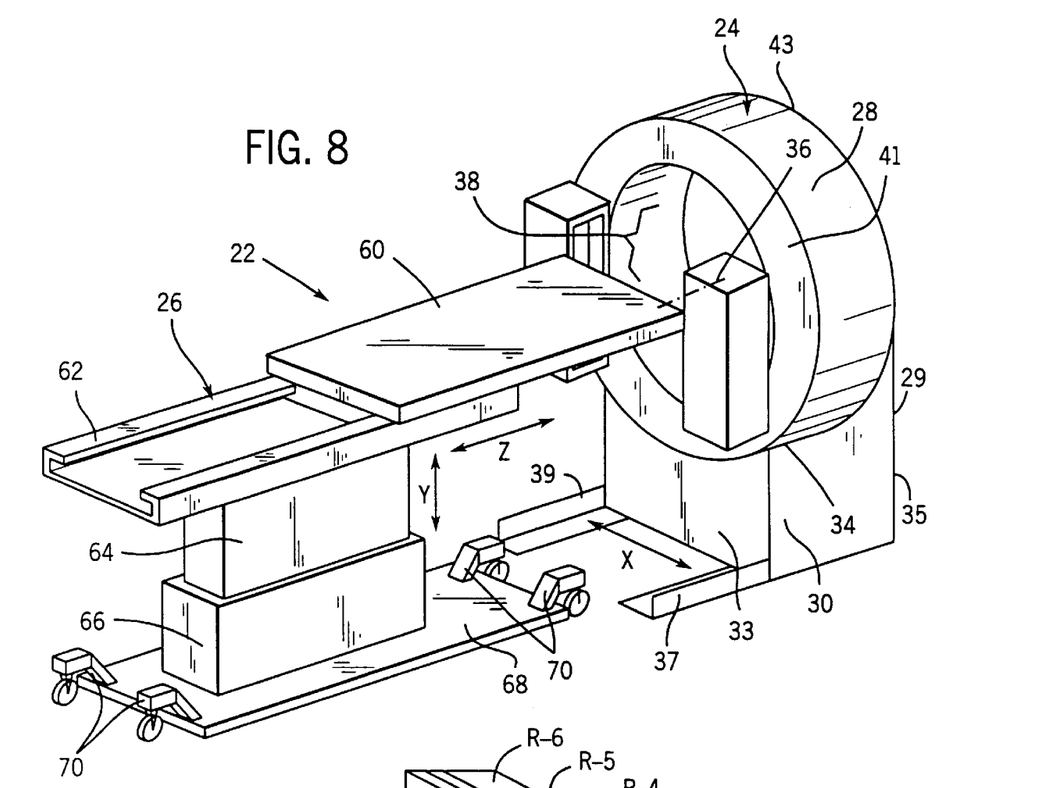
FIG. 8 is a perspective view of an imaging system employing the present invention.

Referring now to FIG. 8, there is shown, generally at 22, an imaging system including a tomography machine 24 and a patient support table 26.

The support table 26 includes a top surface 60 interleaved to a lower bracket member 62 which allows supported movement of the top surface 60 along a horizontal Z-axis. The bracket member 62 is supported by a vertical leg 64 which extends upwardly from a collar 66. The length of leg 64 can be increased or decreased to raise or lower top surface 60 along a vertical Y-axis. Collar 66 is secured to a planar dolly 68 having four wheels collectively identified by the numeral 70, one wheel 70 attached at each of four corners. The wheels 70 allow an operator to move the entire table 26 laterally along an X-axis or along the Z-axis. Thus, the table 26 allows an operator to move the top surface 60 and a patient thereon within a range of three dimensional space.

The tomography machine 24 includes a pedestal 30, a gantry 28 and two planar gamma cameras 32, 34. The pedestal 30 has a front end 33 and a back end 35 and includes two stabilizing legs 37, 39 which extend forward from the front end 33, distal ends of the legs 37, 39 contacting a ground surface in front of the pedestal to stabilize the pedestal front end 33 as the tomography machine 24 is generally front end heavy. The top surface of the pedestal 30 is generally shaped concavely upward so as to receive an outer surface of gantry 28. In addition, although not shown, the pedestal 30 may also house a gantry motor for rotating the gantry 28 about a central gantry rotation axis 36.

The gantry 28 is generally doughnut shaped about the central rotation axis 36. The pedestal 30 supports the gantry 28 in an upright vertical orientation so that its rotation axis 36 is horizontal and can be parallel to the support table Z-axis. The gantry 28, like the pedestal 30, has a front end and a back end defined by front and back surface 41 and 43, respectively. The gantry 28 ideally can rotate about central rotation axis 36 through 540° of rotation and, at a minimum, to produce 360° imaging, must be able to rotate through 180°.

Figure 9:
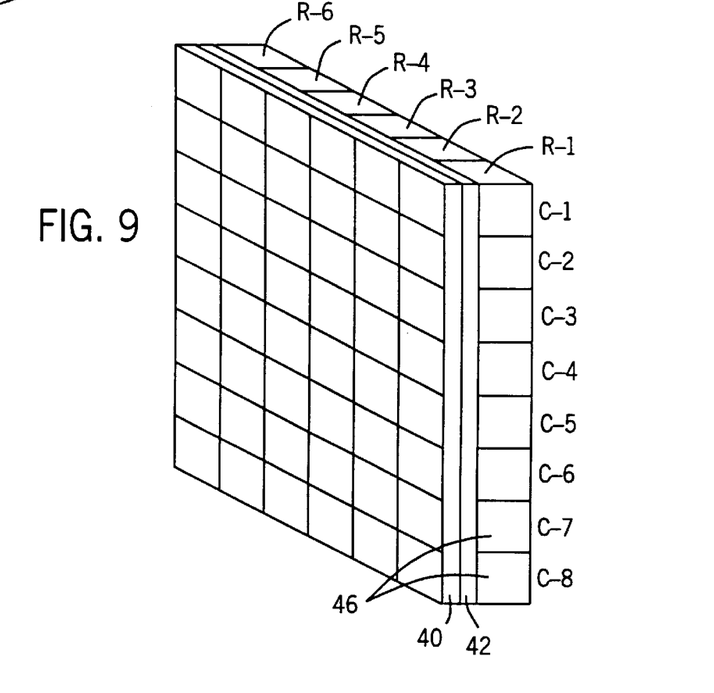
FIG. 9 is a perspective view of a gamma detector.

The two gamma emission cameras 32, 34 are mounted securely to the front surface 41 of the gantry 28 so that when the gantry 28 rotates about axis 36, the cameras 32, 34 likewise rotate. Cameras 32, 34 are used to detect and identify coordinates of gamma emissions. Referring also to FIG. 9, each camera 32, 34 includes a lead plate 40 that defines a myriad of fine holes perpendicular to its length so that the plate acts as a collimator defining parallel paths therethrough. A scintillation crystal 42 is positioned behind each collimator 40 which absorbs gamma emissions which pass through the collimator holes perpendicular to the collimator's length and produce light emissions corresponding to each absorbed gamma emission. The light emissions are directed toward an array of closely packed PMTs which are collectively designated by numeral 46 which form columns C-1 through C-8 and rows R-1 through R-6.

Detected light emissions cause the PMTs 46 to produce analog signals which are sent to controller 16 (FIG. 1) which uses the signals to generate the coordinates of each photon absorbed according to the inventive method.

Figure 10:
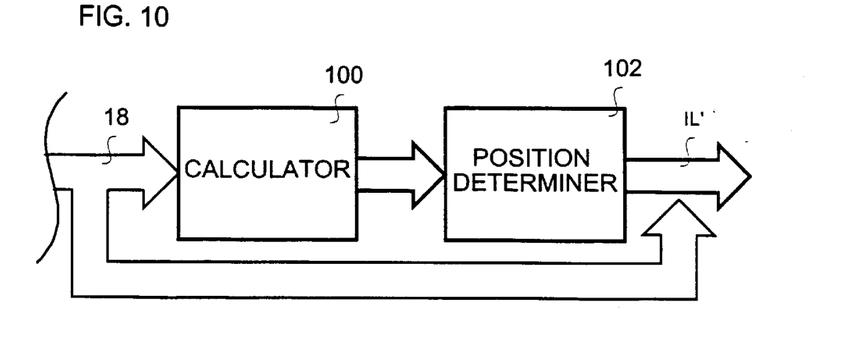
FIG. 10 is a schematic diagram of an apparatus according to the present invention.
Figure 11:
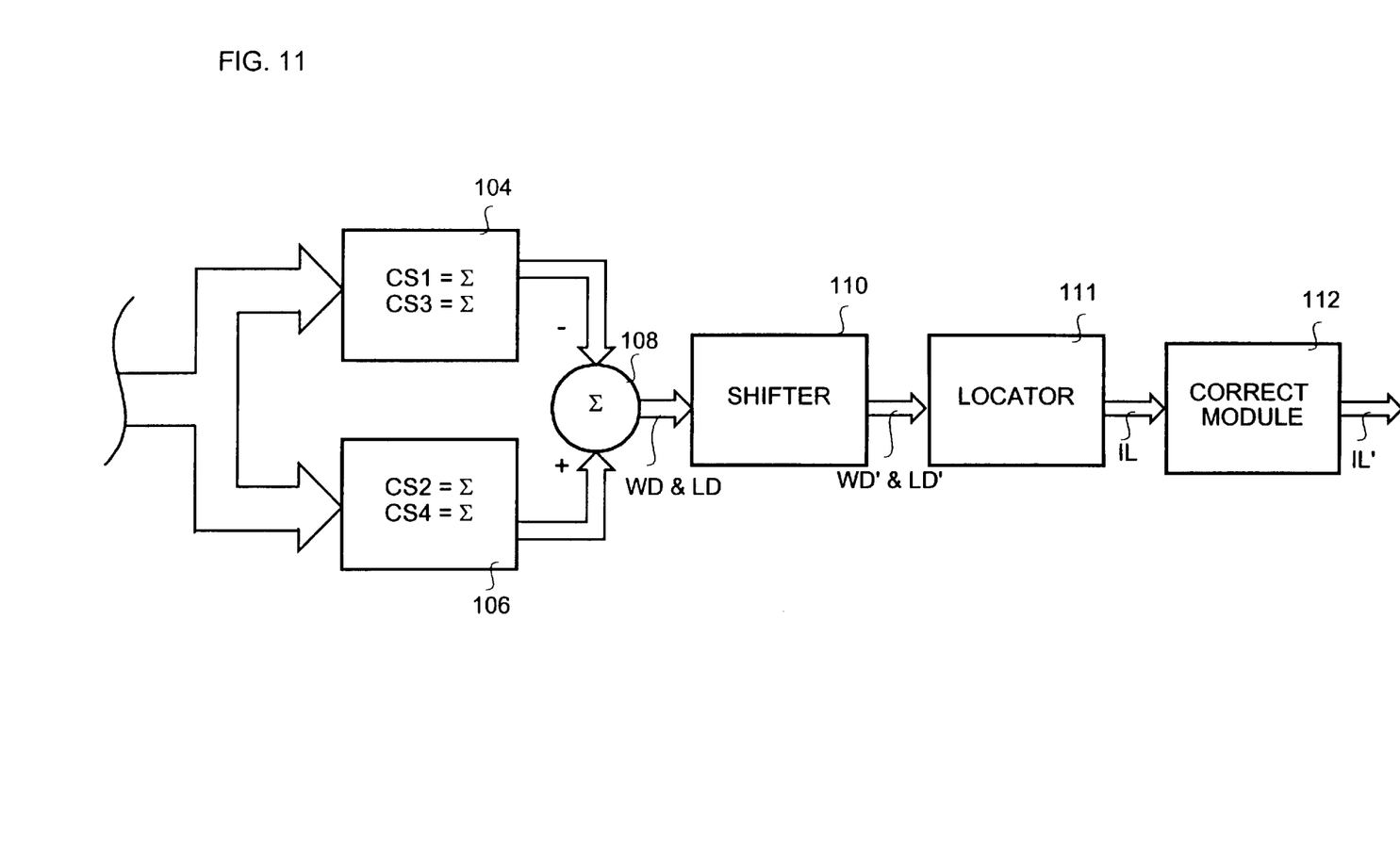
FIG. 11 is a schematic diagram of the position determiner of FIG. 10.

Referring also to FIGS. 10 and 11, for purposes of implementing the inventive method, controller 16 includes a calculator 100 and a position determiner 102 and determiner 102 includes first, second and third summers 104, 106 and 108, respectively, a shifter 110, a locator 111 and a correction module 112.

D. Operation

In operation, after a suitable radiopharmaceutical has been injected into a patient's blood stream, with the patient (generally 90) resting on top surface 60, the table 26 is manipulated along the X and Y axes until the patient 90 is positioned generally concentrically with the gantry along rotation axis 36. The patient 90 and table 26 are then manipulated along the rotation axis 36 in the Z-axis direction until the portion of the patient to be imaged is located between the two planar gamma cameras 32, 34 within the imaging area 38. When properly positioned, the table 26 is locked in place so that it will not move with respect to the tomography machine 24 during imaging. After the time required for the radiopharmaceutical to become concentrated in the organ to be imaged, imaging begins.

Figure 12:
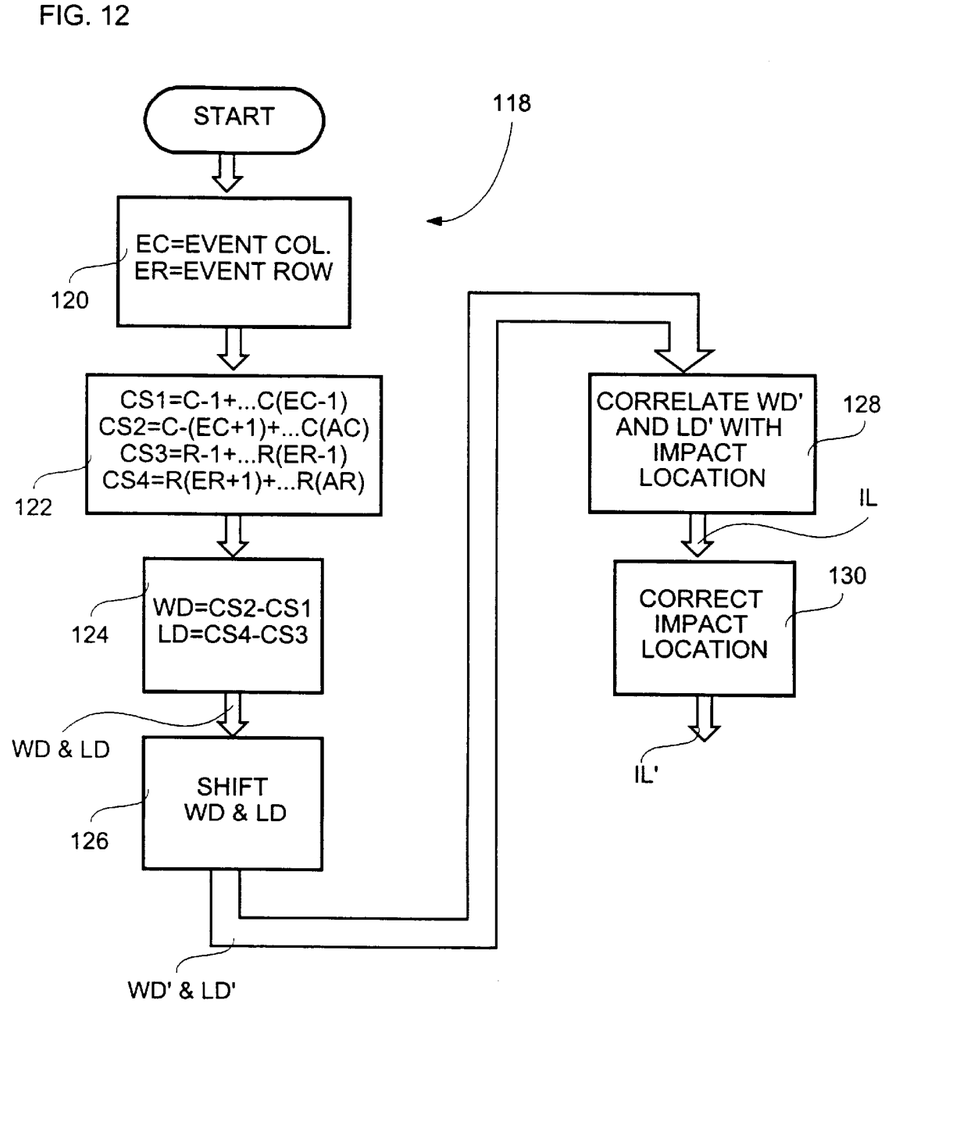
FIG. 12 is a flow chart illustrating operation of the determiner of FIG. 11.

Referring to FIG. 12, an impact location process 118 is illustrated. Referring also to FIG. 10, at process block 120, calculator 100 receives all PMT intensity signals via bus 18 and determines an event column EC and event row ER using the row/column method described above. The event row ER and event column EC are the row and column of a PMT which has an impact location for a specific photon. The process of determining the event row ER and event column EC via the row/column method described above is well known to those skilled in the art and therefore will not be explained here in detail.

The event row ER and event column EC are provided to determiner 102, which also receives the PMT intensity signals via bus 18. Referring to FIGS. 11 and 12 at process block 112, summer 104 adds up all PMT intensity signals in columns to the left (to a first side) of event column EC generating a first composite signal CS1 and adds up all PMT intensity signals in rows above (to a first side) of event row ER generating a third composite signal CS3. Similarly, at step 122, summer 106 adds up all PMT intensity signals in columns to the right (to a second side) of event column EC generating a second composite signal CS2 and adds up all PMT intensity signals in rows below (to a second side) of event row ER generating a fourth composite signal CS4. Composite signals CS1, CS2, CS3 and CS4 are provided to summer 108 which subtracts signal CS1 from signal CS2 providing a width field differentiated signal WD and subtracts signal CS3 from signal CS4 providing a length field differentiated signal LD at process block 124.

Differentiated signals WD and LD are provided to shifter 110 which, at block 126, shifts the signal intensity up or down depending upon which row and column are the event row and columns, ER, EC, respectively. For example, referring again to FIGS. 6 and 7, because segment 54 was shifted down by 130 IU to generate width curve 86, if column C-4 (which corresponds to segment S-4 and shifted segment S-4') is the event column EC, shifter 110 would shift signal WD down by 130 IU providing shifted differentiated width signal WD'. Similarly, if column C-2 is the event column, because segment S-2 (FIG. 6) was shifted down by 650 IU to generate segment S-2' (FIG. 7), signal WD would be shifted down by 650 IU providing shifted signal WD'. Signal LD is similarly shifted as a function of which row is the event row ER and the amount of offset which was required to provide the length curve (not illustrated). Shifted signals WD' and LD' are provided to locator 111.

Locator 111 includes both the width curve (FIG. 7) and length curve (not illustrated) for the detector in some form accessible for correlation purposes. To this end, locator 111 may include a width look-up table and a separate length look-up table which correspond to the width and length curves, respectively. At process block 128, locator 111 correlates signal WD' with a location in the width curve and correlates signal LD' with a location in the length curve. The two locations together provide an estimated impact location IL which is provided to correction module 112.

Module 112 preferably includes a look-up table which correlates estimated impact locations IL within the detector field with corrected impact locations. In other words, this table includes the data generated during the second portion of the commissioning procedure. At block 130, module 112 correlates the estimated impact location IL with the correct location IL' and generates an actual impact location IL' for the photon.

An example of how controller 16 operates would be instructive. Referring again to FIG. 1, assuming an impact location at point 12 of PMT C-4, R-4, signal intensities will again be assumed to be as illustrated. Referring also to FIGS. 10 and 12, calculator 100 receives all intensity signals via bus 18 and, at block 120 determines the event column is C-4 and the event row is R-4. Referring also to FIG. 11, at block 122, summer 104 adds intensity signals from columns to the left of column C-4 (i.e., columns C-1 through C-3) generating first composite signal CS1 (i.e., CS1=C-1= . . . C(EC−1). Here, signal CS1 is 123 IU. Summer 106 adds intensity signals from columns to the right of column C-4 (i.e., columns C-5 through C-8) generating second composite signal CS2 (i.e., CS2=C(EC+1)+ . . . C(AC), where AC is the total number of columns). Signal CS2 is 34. Likewise, at block 122, summers 104 and 106 also generate signals CS3 and CS4 as described above.

Next at block 124, summer 108 subtracts signal CS1 from signal CS2 generating differentiated width signal WD (and also generates signal LD). Here, signal WD is $^-$89. At block 126, shifter 110 shifts signal WD so that the resulting signal corresponds to the data in FIG. 7. Because segment S-4 was shifted down 130 IU to generate segment S-4', signal WD is shifted down 130 IU producing a shifted signal WD'=$^-$89−130=$^-$219.

At block 128, locators 111 correlates WD' with the field curve in FIG. 7 and also correlates LD' with the length field curve generating estimated impact location IL'.

In FIG. 7, signal WD'=$^-$219 corresponds to a detector width position of 205 mm from the left most edge of the 540 mm detector field. Because the 540 mm field begins at a 50 mm mark from the left most edge of column C-1, position 195 mm corresponds to 255 mm from the left most edge of the detector array 10. A similar position signal LD' is derived. The two signals WD' and LD' together provide the estimated impact location IL.

At block 130, module 112 correlates estimated impact location IL with a correct location and provides actual location IL'.

It will be apparent to those of ordinary skill in the art from the above description that many variations are possible from the preferred embodiments. For example, referring to FIGS. 6 and 7, while segments S-2 through S-7 where offset to generate segments S-2' through S-7' and then shifter 110 (FIG. 10) was required to offset differentiated signals WD' and LD' in order to use curve 86 (and the length curve), clearly the offsetting in both commissioning and actual imaging could be eliminated to provide a simpler protocol whereby location within a detector is determined. Also, the invention is meant to include other methods whereby more than two rows or two columns of intensity signals are combined to determine an impact location. For example, four columns instead of seven columns might be used to locate an impact location within a PMT's width. In addition, the actual mathematics used to combine signals might be different, the important aspect of this invention being that nearly all intensity data is used to improve photon statistics and thereby improve SPECT imaging.

In order to apprise the public of the various embodiments that may fall within the scope of the invention, we make the following claims.

We claim:

1. A method to be used with a gamma camera, the camera including a scintillation crystal having opposite impact and emitter sides and a plurality of light detecting photo multiplier tubes (PMTs), each PMT having a width and a length and arranged end to end along their widths in Y rows forming X columns on the emitter side, the crystal positionable adjacent an imaging area such that photons from within the imaging area impact the impact side, each photon which impacts the impact side impacting the side at a specific impact point adjacent a specific impact location on an event PMT, when a photon impacts the crystal, the crystal emitting light from the emitter side adjacent the impact point, the PMTs sensing emitted light and generating intensity signals related to each impacting photon, the method for determining where an impact location occurs along an event PMT's width, the method comprising the steps of, when a photon impacts the crystal:

(a) determining the event PMT;
   (b) determining an event column, the event column being the column in which the event PMT is located;
   (c) mathematically combining the intensity signals of all PMTs to a first side of the event column providing a first composite signal;
   (d) mathematically combining the intensity signals of all PMTs to a second side of the event column providing a second composite signal; and
   (e) comparing the first and second composite signals to determine the impact location along the width of he event PMT.

2. The method of claim 1 wherein the method is also for determining where an impact location occurs along the event PMT's length, the method further including the steps of, after determining the event PMT:

(f) determining an event row, the event row being the row in which the event PMT is located;
   (g) mathematically combining the intensity signals of all PMTs on a first side of the event row providing a third composite signal;
   (h) mathematically combining the intensity signals of all PMTs on a second side of the event row providing a fourth composite signal; and
   (i) comparing the third and fourth composite signals to determine the impact location along the width of the event PMT.

3. The method of claim 1 wherein the total widths of the PMTs form a width field and the step of comparing the first and second composite signals includes the steps of subtracting the first composite signal from the second composite signal to produce a total signal and correlating the total signal with a field position in the width field to determine an impact location estimate along the width of the event PMT.

4. The method of claim 3 further including the step of, after the impact location estimate is determined, determining a correction value for the location estimate and adjusting the location estimate as a function of the correction value.

5. The method of claim 1 wherein the steps of mathematically combining are adding steps.

6. The method of claim 2 wherein the steps of mathematically combining are adding steps.

7. The apparatus of claim 3 wherein the step of correlating includes the step of comparing the total signal to values in a look-up table.

8. An apparatus to be used with a gamma camera, the camera including a scintillation crystal having opposite impact and emitter sides and a plurality of light detecting photo multiplier tubes (PMTs), each PMT having a width and a length, the PMTs arranged end to end along their widths in Y rows forming X columns on the emitter side, the crystal positionable adjacent an imaging area such that photons from within the imaging area impact the impact side, each photon which impacts the impact side impacting the side at a specific impact point adjacent a specific impact location on an event PMT, the event PMT being the PMT having the impact point associated with a specific photon, when a photon impacts the crystal, the crystal emitting light from the emitter side adjacent the impact point, the PMTs sensing emitted light and generating intensity signals related to each impacting photon, the apparatus for determining where an impact location occurs along an event PMT's width, the apparatus comprising:
- a calculator for determining an event PMT and an event column, the event column being the column in which the event PMT is located;
- a first summer for mathematically combining the intensity signals of all PMTs to a first side of the event column providing a first composite signal;
- a second summer for mathematically combining the intensity signals of all PMTs to a second side of the event column providing a second composite signal; and
- a comparator for comparing the first and second composite signals to determine the impact location along the width of the event PMT.

9. The apparatus of claim 8 wherein the apparatus is also for determining where an impact location occurs along an event PMT's length, the comparator being a first comparator and the calculator also identifying an event row, the event row being the row in which the event PMT is located, the apparatus further comprising:
- a third summer for mathematically combining the intensity signals of all PMTs on a first side of the event row providing a third composite signal;
- a fourth summer for mathematically combining the intensity signals of all PMTs on a second side of the event row providing a fourth composite signal; and
- a second comparator for comparing the third and fourth composite signals to determine the impact location along the length of the event PMT.

10. The apparatus of claim 8 wherein the calculator is a first calculator, the total widths of the PMTs form a width field and the comparator includes a second calculator for mathematically combining the first and second composite signals to produce a total signal and correlating the total signal with a field position to determine an impact location estimate along the width of the event PMT.

11. The apparatus of claim 10 wherein the second calculator includes a look-up table which correlates total signal values and impact location estimates and the second calculator correlates by accessing the look-up table.

12. The apparatus of claim 10 wherein the second calculator mathematically combines the first and second composite signals by subtracting the first signal from the second signal.

13. The apparatus of claim 8 wherein the first and second summers mathematically combine by adding.

14. The apparatus of claim 9 wherein the summers mathematically combine by adding.

15. The apparatus of claim 12 further including a correction module which, after the impact location estimate is determined, determines a correction value for the location estimate and adjusts the location estimate as a function of the correction value.

16. A method to be used with a gamma camera signal processor, the camera including a scintillation crystal having opposite impact and emitter sides and at least X by Y light detecting photo multiplier tubes (PMTS) arranged end to end along PMT widths in X columns and Y rows on the emitter side, the total width of the PMTs in a row defining a view width, the crystal positionable adjacent an imaging area such that photons from within the imaging area impact the impact side at specific impact points adjacent specific impact locations on the PMTs, when a photon impacts the crystal, the crystal emitting light from the emitter side adjacent the impact point, the PMTs sensing emitted light and generating intensity signals related to each impacting photon, the method for calibrating the signal processor to correlate signal intensities with impact locations within an event PMT's width, an event PMT being the PMT adjacent an impact point, the method comprising the steps of:
- (a) moving a photon point source from one end of the view width to the other;
- (b) detecting and recording signal intensities as a function of point source location along the view width providing a separate intensity curve for each PMT;
- (c) adding up the signal intensities in each column generating a separate column intensity signal for each column;
- (d) for at least each individual column in the subset of columns consisting of the second through the (X-1)th, generating a differentiated curve consisting of all intensity curves corresponding to columns to a first side of the individual column being subtracted from all intensity curves corresponding to columns to a second side of the individual column;
- (e) choosing segments of each differentiated curve which are essentially the same width as corresponding PMTs to be discriminated segments; and
- (f) offsetting the discriminated segments to provide an essentially continuous field width curve.

17. The method of claim 16 wherein the total lengths of the PMTs in each of the Y rows define a field of view length, the method further comprising the steps of:
- moving the photon point source from one end of the view length to the other;
- detecting and recording signal intensities as a function of point source location along the view length providing a separate intensity curve for each PMT;
- adding up the signal intensities in the separate rows to generate row signal intensities;
- for at least each individual row in the subset of rows consisting of the second through the Y-1 rows, generating a differentiated curve consisting of all intensity curves corresponding to rows to a first side of the individual row being subtracted from all intensity curves corresponding to rows to a second side of the individual row;
- choosing segments of each differentiated curve which are essentially the same length as corresponding PMTs to be discriminated segments; and
- offsetting the discriminated segments to provide an essentially continuous field length curve.

* * * * *